United States Patent [19]

Avery et al.

[11] Patent Number: 5,019,590

[45] Date of Patent: May 28, 1991

[54] ANTIMALARIAL ANALOGS OF ARTEMISININ

[75] Inventors: Mitchell A. Avery, Palo Alto; Wesley K. M. Chong, Mountain View, both of Calif.

[73] Assignee: SRI International, Menlo Park, Calif.

[21] Appl. No.: 414,730

[22] Filed: Sep. 27, 1989

Related U.S. Application Data

[63] Continuation of Ser. No. 108,145, Oct. 13, 1987, abandoned, which is a continuation-in-part of Ser. No. 943,555, Dec. 12, 1986, abandoned.

[51] Int. Cl.$^5$ .................. A61K 31/365; C07D 493/18
[52] U.S. Cl. ..................................... 514/450; 514/453; 549/276; 549/277; 549/279; 549/348; 568/374; 556/489; 556/436
[58] Field of Search ..................... 549/276, 279, 348; 514/450

[56] References Cited

U.S. PATENT DOCUMENTS 4,350,638  9/1982  Lee .................................... 549/275

OTHER PUBLICATIONS

Song CA 103:205354K
Xu CA 99:158654V
Yu. CA 95:150917e
Li. CA 98:4420h
Wang CA 94:90114h
Buchi et al., (1978) Journal of the American Chemical Society 100:294–295.
Still (1976) Synthesis 7:453–454.
Taguchi et al., (1973) Journal of the American Chemical Society 95:7413–7418.
Warnhoff et al., (1967) Journal of Organic Synthesis 32:2664–2669.
Klayman (1985) Science 228:1049–1055.
Klayman (1979) Chinese Medical Journal 92:811–816.
Zhou (1986) Pure and Applied Chemistry 58:817–824.
Schmid et al., (1983) Journal of the American Chemical Society 105:624–625.
Avery et al., (1987) Tetrahedron Letters 28:4629–4632.
Clark et al., (1985) J. Org. Chem. 50:1994–1996.
Rosch et al., (1981) Angew. Chem. Int. Ed. Engl. 20:581–582.
Xing-Xiang et al., (1986) Tet. Lett. 42:819–828.
Ireland et al., (1984) Journal of the American Chemical Society 106:3668–3670.

Primary Examiner—Jane T. Fan
Attorney, Agent, or Firm—Richard P. Lange

[57] ABSTRACT

A process for synthesizing oxygen-containing polyoxatetracycle compounds and in particular analogs of the antimalarial agent known as qinghaosu or artemisinin is disclosed. The process employs as a reactant an olefinically unsaturated bicyclic bridging ketone having nonenolizable bridgehead moieties for both of its alpha positions. This ketone is converted to a vinylsilane that is subjected to ozonolytic cleavage of its olefinic bond to yield a member of a family of unique carboxyl/carbonyl-substituted vinylsilanes which may in turn optionally be subjected to a wide range of reactions prior to a final ozonolysis/acidification step which closes the oxygen-containing ring structure. The various intermediates are claimed as aspects of this invention as are novel tetracycles and their use as antimalarials.

9 Claims, 5 Drawing Sheets

Figure 1 continued on next page

ANTIMALARIAL ANALOGS OF ARTEMISININ

This invention was made during the performance of a contract from the United States Government, Department of the Army. The government has rights under this invention.

REFERENCE TO RELATED APPLICATION

This application is a continuation of Ser. No. 07/108,145 filed Oct. 13, 1987 now abandoned which is a continuation-in-part of U.S. patent application Ser. No. 943,555, filed Dec. 12, 1986 now abandoned.

BACKGROUND OF THE INVENTION

1. Field of the Invention

This invention is in the field of organic chemistry. More particularly, it relates to a process for the synthesis of oxygen-containing heterocyclic organic compounds, materials formed by this process, and intermediates generated in the process. In one application, this process is used to prepare analogs of the antimalarial agent known as qinghaosu or artemisinin.

2. Background References

In prior copending U.S. patent application Ser. No. 943,555, there is disclosed a multi-step stereospecific synthesis of the oxygen-containing tetracycle artemisinin and a group of its analogs.

We have now found a new process for producing such materials. This new process is characterized by being a more direct route and by achieving the desired analogs in several fewer steps. It is also characterized by improved versatility which permits the synthesis of a wider range of possible analogs.

The present process employs ozonolysis of vinylsilanes to introduce oxygen functionality. A reference of which we are aware which involves ozonolysis of a vinylsilane is that of George Buchi et al., *Journal of the American Chemical Society*, Vol 100, 294 (1978). This reference illustrates the use of this reaction but effects different rearrangements and arrives at different ring structures than called for herein.

In another aspect, this invention employs unsaturated bicyclic ketones as reactants. References relating to such materials and to methods for forming some of them include W. Clark Still, *Synthesis*, Number 7, 453–4 (1976); Kazuo Taguchi et al., *Journal of the American Chemical Society*, Vol. 95, 7313-8 (1973); and E. W. Warnhoff et al., *Journal of Organic Synthesis*, Vol 32, 2664–69 (1967).

Other art of interest to the present invention relates to the ancient antimalarial natural product known as qinghaosu. The antimalarial qinghaosu has been used in China in the form of crude plant products since at least 168 B.C. Over the last twenty years, there has been an extensive interest in this material. This has led to an elucidation of its structure as The chemical name artemisinin has been applied to the material. This name will be used in this application to identify the material.

The carbons in the artemisinin structure have been numbered as set forth above. When reference is made to a particular location in a compound of this general type, it will, whenever possible, be based on the numbering system noted in this structure. For example, the carbon atoms bridged by the peroxide bridge will always be identified as the "4" and "6" carbons, irrespective of the fact that this invention can involve materials having different bridge-length structures in which these carbons would otherwise be properly numbered.

References to artemisinin and to its derivatives include the May 31, 1985 review article by Daniel L. Klayman appearing in *Science*, Vol 228, 1049 (1985); and the article appearing in the *Chinese Medical Journal*, Vol 92, No. 12, 811 (1979). Two syntheses of artemisinin have been reported in the literature by Wei-Shan Zhou, *Pure and Applied Chemistry*, Vol 58(5), 817 (1986); and by G. Schmid et al., *Journal of the American Chemical Society*, Vol 105, 624 (1983). Neither of these syntheses employs ozonolysis or the unsaturated bicyclic ketones as set forth herein.

The interest in artemisinin has prompted a desire for an effective and efficient method for its synthesis and for the synthesis of its analogs. It is also of interest to be able to apply such a method to the production of other oxygen-containing tetracycles. The prior application provided one such method. This invention provides an additional method.

STATEMENT OF THE INVENTION

A new process for forming tetracyclic oxygen-containing compounds has now been found. The process is characterized by employing as a reactant an olefinically unsaturated bicyclic bridging ketone having nonenolizable bridgehead moieties for both of its alpha positions (that is, at the positions immediately adjacent to the carbonyl). The process is further characterized by converting this ketone carbonyl to a vinylsilane. This vinylsilane is then subjected to ozonolytic cleavage of its olefinic bond to yield a member of a family of unique carboxyl/carbonyl-substituted vinylsilanes which may in turn optionally be subjected to a wide range of reactions prior to a final ozonolysis/acidification step which closes the oxygen-containing ring structure. This process can yield desired artemisinin (qinghaosu) analogs and the like in several fewer steps than prior processes. It can also give rise to a variety of artemisinin analogs not easily obtainable with the prior processes. The process is also characterized by permitting control of the stereochemistry of the "1", "4", "5", "6", and "7" centers (as these positions are defined in artemisinin).

Thus, in one aspect this invention provides a family of new bicyclic bridging ketones of General Formula I General Formula I wherein m is an integer—either 0 or 1; n is an integer—either 0, 1, 2, 3, or 4; and the various R's are each independently selected from hydrogens, alkyls and substituted alkyls.

In another aspect, this invention provides the corresponding family of vinylsilanes of General Formula II General Formula II wherein m, n, and the various R's each have the meanings ascribed to them with reference to General Formula I and the three $R^S$'s each are lower hydrocarbyls. These materials can be formed by silylating the ketones of General Formula I.

The alkylene olefinic bond in the vinylsilanes of General Formula II undergoes a suprisingly preferential ozonolytic cleavage (the olefinic bond in the vinylsilane functionality is not significantly attacked) to yield the mixed carbonyl/ester vinylsilanes of General Formula III.

General Formula III

These materials, wherein m, n, the R's, and the $R^S$'s each have the meanings ascribed to them with reference to General Formula II and $R^E$ is a protecting esterifying group such as a lower alkyl, constitute another aspect of this invention. The materials of General Formula III are very versatile. Following deprotection of the acid functionality, they can be subjected to further ozonolysis and acid treatment to yield tetracyclic artemisinin analogs directly. Alternatively, with their acid functionality protected, they can have their carbonyl-containing chain extended by classic chain extension techniques such as by the Wittig reaction. These chain extension products can be represented by General Formula IV.

General Formula IV

In General Formula IV the chain extension is represented by the unit wherein R is a hydrogen, an alkyl or a substituted alkyl and p is an integer of from 0 to 2 subject to the proviso that p plus m has a value not greater than 2. In General Formula IV, the remaining R's and $R^S$'s and $R^E$ and m and n have the meanings previously ascribed to them with reference to Formula III.

The chain extension produucts can be deprotected and then can be subjected to ozonolysis and acidification to form the desired tetracyclic structure. In another variation, the acid functionality and the carbonyl functionality can be protected (such as by esterification and by conversion to an acetal or ketal, respectively) and the product then alkylated to add an $R^F$ group and deprotected to give a product as shown in General Formula V.

General Formula V

In the formula $R^F$ is a lower alkyl group or substituted lower alkyl group and the other substituents are as previously defined. This alkylation product is then subjected to ozonolysis and acidification to yield the desired tetracycle.

Of course, one could alter the sequence of these several steps or alternatively employ more than one of these modifications.

As previously noted, the materials of General Formulas III, IV or V can be subjected to ozonolysis and acidification to create a final tetracycle. Such tetracycles are represented by General Formula VI.

General Formula VI

In this formula, X and Y together can equal a carbonyl oxygen or X can be hydrogen, while Y is selected from hydrogen, hydroxyl, or alkyl ethers; carboxylic esters; carbonates, carbamates, amides and ureas. The various other substituents have the meanings previously ascribed to them.

In a further aspect, the present invention provides the process for forming the claimed tetracycles and their intermediates. This process involves the combination of the several steps outlined above.

In additional aspects, the present invention provides pharmaceutical compositions based on these tetracycle compounds and the use of these compositions to treat malaria and other similar conditions.

BRIEF DESCRIPTION OF THE DRAWING

The present invention will be described with reference being made to the accompanying drawing in which.

DETAILED DESCRIPTION OF THE INVENTION

DESCRIPTION OF PREFERRED EMBODIMENTS

Figure 1:
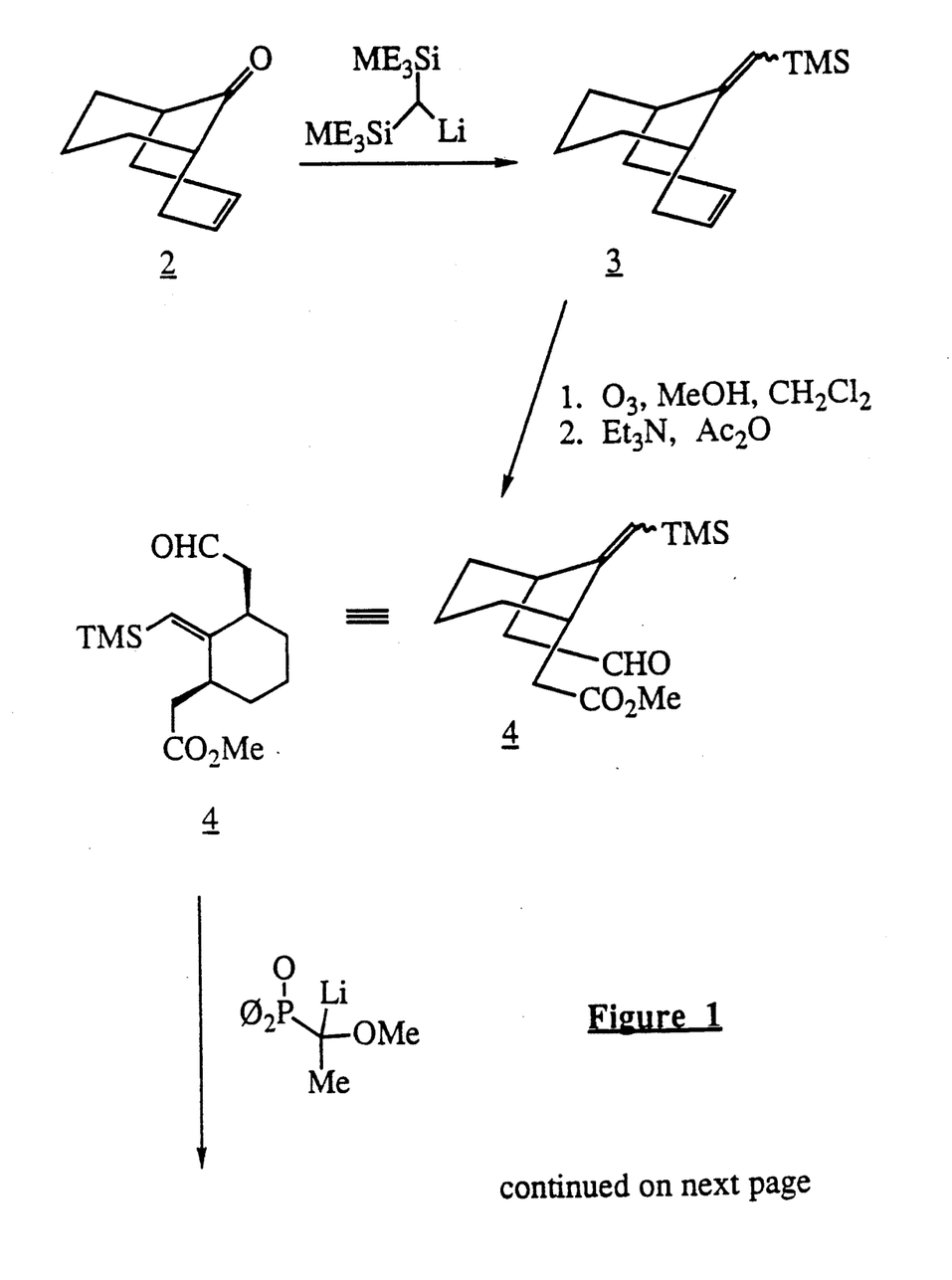
FIG. 1 is a flow scheme illustrating an overall process in accord with this invention.

In accord with this invention, analogs of artemisinin of General Formula VI can be prepared using the general reaction techniques set forth in FIG. 1. Additional variations can be introduced using the techniques of FIG. 2. This reaction sequence proceeds from a bridgehead ketone through a bridgehead vinylsilane through a mixed carbonyl/ester compound to the final tetracycles.

This Description of Preferred Embodiments is arranged in accordance with these various compounds and reactions into the following sections:

1. The Bridgehead Ketones of Formula I
2. The Vinylsilanes of Formula II
3. The Mixed Carbonyl/Ester Vinylsilanes of Formula III
4. The Chain-Extended Vinylsilanes of Formula IV
5. The Derivatized Vinylsilanes of Formula V
6. The Tetracycles of Formula VI
7. The Preparation Process
8. Use of the Tetracycles
9. Examples

1. The Bridgehead Ketones of Formula I

The bridgehead ketones which are employed as intermediates in the synthesis scheme of this invention can be defined structurally by means of General Formula I. In this formula m is an integer—either 0 or 1; n is an integer—either 0, 1, 2, 3, or 4; and the various R's are each independently selected from hydrogens, alkyls and substituted alkyls.

In defining the groups represented by the various R's in General Formulas I-VI, reference is made to the possibility of "substituting" these groups. The limits of this possible substituting can be spelled out in functional terms as follows: A possible substituent is a chemical group, structure or moiety which, when present in the compounds of this invention, does not substantially interfere with the preparation of the compounds or which does not substantially interfere with subsequent reactions of the compounds. Thus, suitable substituents include groups that are substantially inert under the various reaction conditions presented after their introduction such as those of ozonolysis. Suitable substituents can also include groups which are predictably reactive under the conditions to which they are exposed so as to reproducibly give rise to desired moieties.

These possible substituents may from time to be referred to as R* such that R's will be described as including one or more R* substituents. R* can be any substituent meeting the above functional definition. Common R* groups include saturated aliphatic groups including linear and branched alkyls of 1 to 12 carbon atoms such as methyl, ethyl, isopropyl, n-butyl, t-butyl, the hexyls including cyclohexyl, decyl and the like. R* can also include aromatic carbon groups generally having from 1 to 10 aromatic carbon atoms, for example aryls such as quinolines, pyridines, phenyls, naphthyls; aralkyls of up to about 20 total carbon atoms such as benzyls, phenylethyls and the like; and alkaryls of up to about 20 total carbon atoms such as the xylyls, ethylphenyls and the like. These various hydrocarbon structures of the R* substituents may themselves include olefinic carbon-carbon double bonds, subject to the understanding that ozonolysis or oxidative cleavage of this unsaturation may occur if it is present during that reaction; amides, sulfonates, carbonyls, carboxyls, alcohols, esters, ethers, sulfonamides, carbamates, phosphates, carbonates, sulfides, sulfhydryls, sulfoxides, sulfones; and nitro, nitroso, amino, imino, oximino, alpha- or beta-unsaturated variations of the above, and the like, subject to the understanding that many of these functional groups may be subject to attack during the overall reaction sequence and thus may need to be appropriately protected. They can then be deprotected at some later stage as desired.

Returning to the materials encompassed by General Formula I, while any of the possibilities encompassed by the formula are possible, preference is given to materials wherein n is 1 or 2 or 3. Preference is also given to materials wherein the various R's are selected from hydrogen, lower alkyls and substituted lower alkyls. As used herein a "lower" group such as an alkyl is one containing from 1 to about 10 and preferably from 1 to about 4 carbon atoms. Materials wherein at most one or two of the R's in the m methylenes and at most one of the R's in the m methylenes are other than hydrogen are especially preferred.

While General Formula I is a very suitable representation of the bridgehead ketones employed herein, and without any intent to limit the scope of the invention beyond the structure so elaborated, at times it may be helpful to the understanding of this invention to provide structures in which the various substituents are distinguished from one another. To that end, General Formula I* is provided to illustrate the location of the various substituents in the bridgehead ketone materials. Other similar expanded formulas will be provided hereinafter for other products and intermediates of the present invention. It should be appreciated that these more elaborate formulas only represent our present best understanding of the structures of these materials and the most likely stereochemistry to the extent known or reasonably inferred. It is possible that inversions may occur at various optically active centers from time to time which are not reflected in these more detailed structures. These additional materials are considered to be part of this invention and to be included within the more general structures such as General Formula I, etc.

General Formula I*

In General Formula I*, m is an integer—either 0 or 1; n is an integer—0, 1, 2, 3, or 4; the m $R^{A1}$'s, $R^{A2}$, $R^{B1}$, $R^{B2}$ and the n $R^{C1}$'s and $R^{C2}$'s are each independently selected from hydrogens, alkyls and substituted alkyls. These various groups have the preferences set forth with reference to General Formula I, as well.

Among the materials encompassed by General Formulas I and I*, several are known compounds. (See Still, supra, for a disclosure of materials wherein n is 1, m is 1 and all the R's are hydrogen; wherein n is 2, m is 1 and all the R's are hydrogen; wherein n is 3, m is 1 and all the R's are hydrogen; and wherein n is 2, m is 1 and all the R's are hydrogen except for one $R^{C1}$, which is a methyl.) The remaining materials are believed to be novel compounds.

The bridgehead ketone materials of General Formulas I and I* can be prepared as follows: When both of the $R^B$ substituents are hydrogen, the materials can be prepared by the cyclodialkylation of appropriate enamines. The pyrrolidine enamines are a well-known family of materials whose preparation from commercial cyclic ketones is well documented, and for this reason they are preferred. In a typical representative reaction cyclohexanone is converted to the cyclohexeneamine, which is then reacted with a 1,4-dichlorobut-2-ene to give a bicyclic ketone as shown in Reaction 1.

Reaction 1

-continued
Reaction 1

In consideration of the chain lengths defined by n and m and the locations of the various R groups, the dialkyation agent can be defined by General Formula VII and the enamine by General Formula VIII. In these formulas, the various R groups have the meanings assigned to them in the previous formulas and the Z's each are leaving groups such as halo's, especially chloro's or bromo's.

General Formula VII

General Formula VIII

These dialkylation agents and enamines can also be represented in the convention of General Formula I* as follows:

General Formula VII*

General Formula VIII*

Figure 3A:
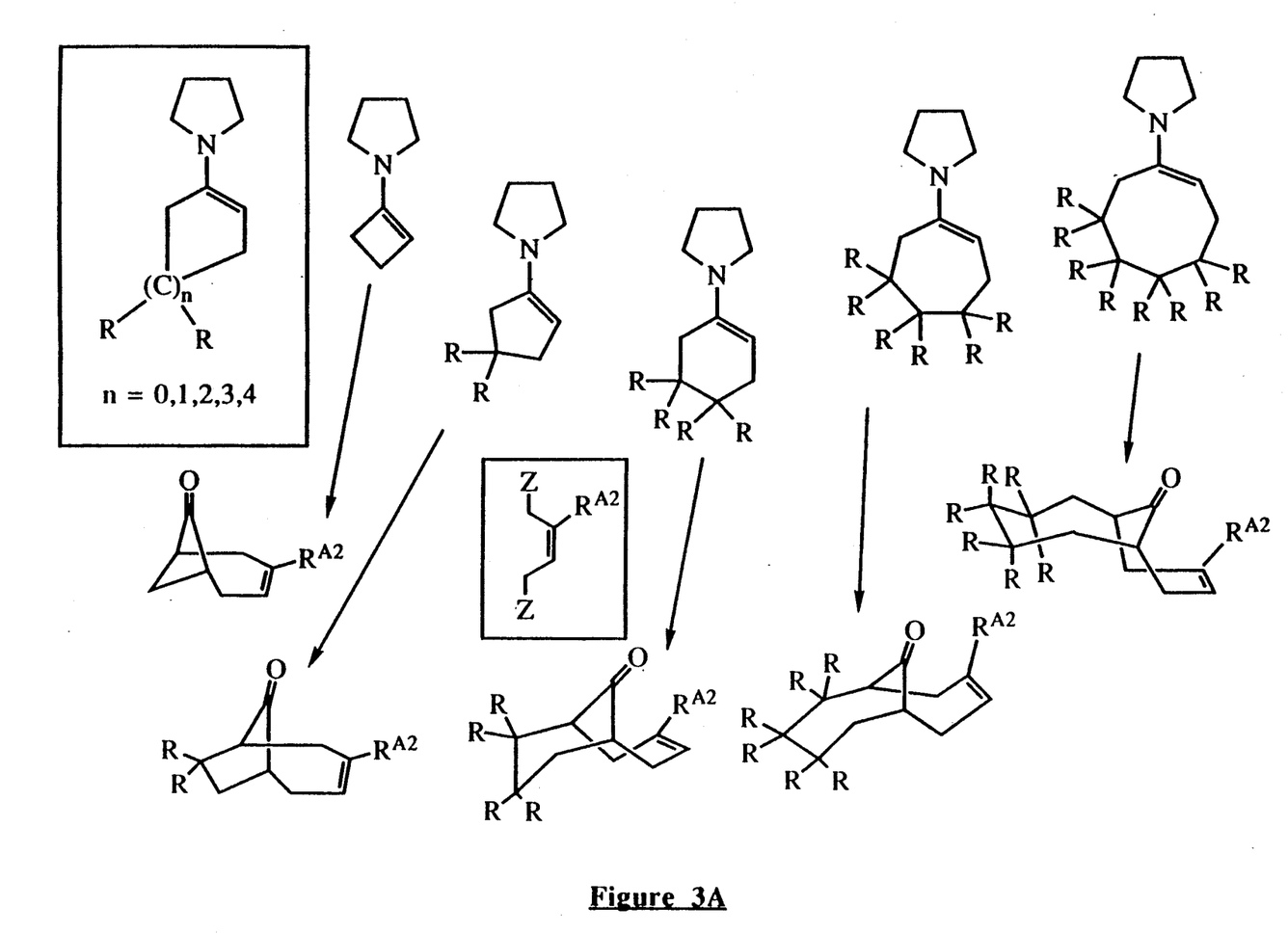
FIGS. 3A and 3B are tables of structures of typical reactants employed as starting materials in the present invention.
Figure 3B:
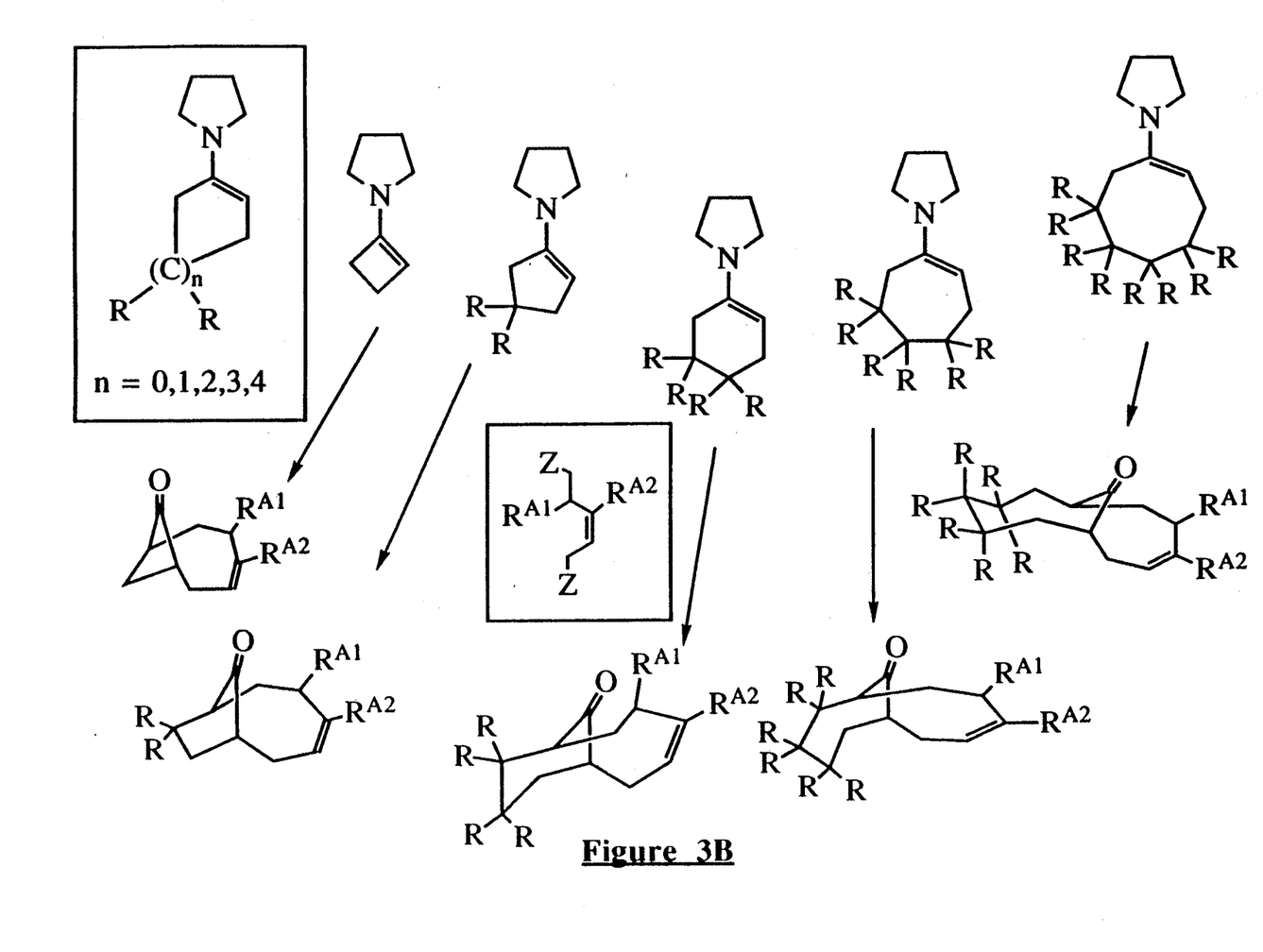

When considering the possible values of n and m, there are two basic structures for the dialkylation agent and five basic structures for the enamine. FIGS. 3A and 3B are tables that grid these materials with one another to illustrate these feedstocks and the ten basic bicycloketone structures to which they give rise.

The reaction of the dialkylation reagent and the enamine is carried out under effective alkylation conditions. These include anhydrous conditions; an aprotic reaction medium such as dimethylformamide, tetrahydrofuran, or the like; and the general exclusion of oxygen from the reaction vessel such as by an inert gas cap. The reaction is generally promoted by the addition of a base such as an amine or the like, for example a trialkyl amine, and by the presence of a halide alkylation promoter such as an alkali metal iodide. In the reaction, approximately equimolar amounts of the dialkylation reagent and the enamine are employed. A representative preparation taken from Still (supra) is provided in Example 1.

In those cases where the bridgehead ketones have $R^B$ substituents other than hydrogen, they can be prepared using the methods set forth by Taguchi et al (supra) and Warnhoff et al (supra). In Taguchi et al saturated bridgehead ketones containing a carboxylic acid functionality at one of the bridgeheads are prepared. The carboxyl group can be used as a point of attachment for other $R^B$ substituents as called for. The Warnhoff et al work discloses a method for introducing carboxyl and halo substituents on both of the bridgehead carbons of saturated bicyclic ketones. Again, these groups can serve as active sites for the coupling of other $R^B$ groups as desired. With suitable modification, the desired olefinic bond can be introduced into the bicyclic structure.

2. The Vinylsilanes of Formula II

The bicyclic bridgehead ketones of Formula I are converted to the vinylsilanes of Formula II. In Formula II the three $R^S$ substituents in the silyl functionality are independently selected from lower hydrocarbyls. Typical hydrocarbyls for this application are lower alkyls, aryls, alkyls and aralkyls. In selecting these three R's, generally two or three of them are methyls. Typical silyl groups include trimethylsilyl, t-butyldimethylsilyl and phenyldimethylsilyl. In preferred silyls, two of the three $R^S$'s are each methyls, and the third is a methyl, ethyl, propyl, butyl, or t-butyl. The various other R's are as described with reference to General Formula I.

Following the conventions set forth defining Formula I*, the vinylsilanes can also be represented by General Formula II*.

General Formula II*

The conversion of the ketone to the vinylsilane can be carried out using any of the art-known methods for silylating a carbonyl functionality. In this case a method which proceeds with good efficiency and yield involves the straightforward use of bis(trialkylsilyl) methyllithium. This reagent can be prepared by the method of Grobel and Seebach, Chem. Ber, 110, 852 (1977), in which an alkyl lithium is reacted with the needed bis(trialkylsilyl)methane in an aprotic dry solvent with hexamethylphosphortriamide at low to moderate temperature to yield the desired reagent complex, which can be used to effect the silylation. The silylation is carried out by contacting the ketone and the silylation reagent at about equimolar levels (0.75 to about 1.33 equivalents of silylation complex based on the ketone present) at low temperatures such as $-100°$ C. to about $0°$ C., once again in an aprotic anhydrous reaction phase. The product of this silyation can be extracted into a nonpolar organic phase and can be worked up by rinsing with water, brine, and the like. The final product can be purified, such as by chromatographic techniques.

3. The Mixed Carbonyl/Ester Vinylsilanes of Formula III

An unexpected and key element of the present invention relates to the formation of the mixed carbonyl/ester vinylsilanes of Formula III (or Formula III*, below) by differential ozonolytic cleavage of the olefinic double bond (instead of the bridging vinylsilane) of Formula II.

General Formula III*

The materials of Formulas III and III* have the same substituents described with reference to the vinylsilanes and additionally include an $R^E$ group which is a protective esterifying group. Typically, $R^E$ is a lower alkyl and especially a methyl but can be any removable carboxyl protecting group as is known in the art.

The ozonolytic cleavage reaction is an adoption of the method described by R. E. Claus and S. L. Schreiber, Org. Syn., 64, 150 (1985). This reaction is carried out at low temperatures in a liquid reaction medium. Ozone is extremely reactive, and it is advantageous to employ low temperatures to avoid side reactions between the ozone and other regions of the vinylsilane molecule. The low temperature can range from a high of about $15°$ C. to a low equal to the freezing point of the reaction solvent, which can be as low as $-100°$ C. or lower. Excellent results are obtained at dry ice/acetone bath temperatures ($-78°$ C.), and a preferred temperature range is from $-100°$ C. to about $-25°$ C. with most preferred temperatures being in the range of from $-70°$ C. to $-80°$ C.

The reaction solvent employed in this reaction is selected to assure compatibility with the highly reactive ozone. As a general rule, ethers, both linear and cyclic, are to be avoided as they are likely to be converted to peroxides, which present an explosion hazard. The solvents employed are commonly mixtures of polar organics, preferably lower alcohols such as methanol, ethanol, the propanols, and ethylene and propylene glycols; and the liquid esters such as ethyl acetate with halohydrocarbons such as methylene chloride, chloroform, dichloroethylene and the like. Of these solvents, the lower alcohols, especially methanol mixed with halohydrocarbons and especially dichloroethylene, are preferred. In the case shown in FIG. 1 and demonstrated in the examples, an optimum solvent was a 5:1 volume ratio of methylene chloride and methanol, respectively. The solvent plus the presence of an acid acceptor such as alkali metal carbonate or bicarbonate gave best results. This acid acceptor is useful t prevent the alcohol of the reaction medium from combining with an aldehyde of the reaction product. The acid acceptor can be employed to advantage if, as in the case of FIG. 1, this reaction is undesired.

The reaction is carried out by mixing the vinyl silane in the reaction medium and then adding the ozone. The amount of ozone preferably is controlled so that excesses are avoided. Good results are obtained when the amount of ozone is limited to not more than 1.25 equivalents, based on the amount of vinylsilane present, with ozone levels of from about 0.75 to about 1.25 equivalents based on the amount of vinylsilane present being preferred. Lower ozone levels can be used, but are not preferred because of the lower yields which result.

The reaction is very quick, generally being complete in a few minutes. Excellent results are obtained, at times in the range of 15 seconds to about 45 minutes depending upon the rate of ozone delivery.

The product of the ozonolytic cleavage can be worked up and recovered. In the case of sensitive products, the workup is carried out under reductive conditions, for example in the presence of an alkylamine and an anhydride such as acetic anhydride. In cases where the product is less sensitive, the conditions need not be reductive.

The recovered product can then be treated with a strong acid such as a mineral acid and preferably hydrochloric acid to yield the tetracycles of Formula VI. This product can be recovered by extraction into an organic layer which is then washed, dried and, if desired, subjected to column chromatography and the like. The mixed carbonyl/carboxyl material is generally unstable and must be used promptly to avoid yield loss.

4. The Chain-Extended Vinylsilanes of Formula IV

Notwithstanding their reactivity, the vinylsilanes of Formula III are versatile intermediates. The carbonyl-containing arm can be extended using conventional chain-extension techniques such as the Wittig reaction. An embodiment of this reaction is shown in FIG. 1 and in the Examples. This serves to introduce a unit wherein R is a hydrogen, an alkyl or a substituted alkyl and p is an integer of from 0 to 2, subject to the proviso that p plus m has a value not greater than 2. Generally it is preferred if at least one of the R groups and particularly 2 or more of the R groups in the chain extension region is hydrogen(s) It is also preferred if the alkyls and substituted alkyls are lower alkyls. The product of this chain extension has the structure shown in Formula IV. Using the convention of Formula I*, these materials can also be represented by General Formula IV*.

General Formula IV*

These chain extension products can be deprotected and subjected to ozonolysis and acidification to yield the desired tetracyclic structure. Alternatively, the chain-extension products can be further derivatized as shown below.

5. The Derivatized Vinylsilanes of Formula IV

After protecting the carbonyl group such as an acetal or ketal, these materials can be derivatized to modify their structure and give rise to numerous other substitution patterns. In another variation, the acid functionality and the carbonyl functionality can be protected (such as by esterification and by conversion to an acetal or ketal, respectively) and the product then alkylated to add an $R^F$ group and deprotected to give a product as shown in General Formula V and (General Formula V* below).

General Formula V*

In this formula the $R^F$ group is a lower alkyl or substituted lower alkyl.

6. The Tetracycles of Formula VI

The artemisinin analog compounds which are provided by this invention are tetracycles which can be defined structurally by means of General Formula VI (or General Formula VI*, below).

General Formula VI*

These compounds are formed from the vinylsilane of Formula III, the chain-extended vinylsilane of Formula IV, or the derivatized vinylsilane of Formula V by ozonolysis and acidification. The substituents are the same as described with reference to the prior structures. The product of the ozonolysis and acidification will have X and Y as a carbonyl oxygen. As will be noted, this carbonyl can be reduced and reacted so that X is hydrogen, while Y is selected from hydrogen, hydroxyl, alkyl ethers, carboxylic esters, carbonate, carbamates, amides and ureas.

It will be appreciated that General Formula VI can be written in simplified forms depending whether or not the chain extension and/or alkylation have taken place. Formula VIA represents the tetracyle which is obtained if the product of Formula III is converted directly, VIB results if a chain extension product is converted, and VIC results if an alkylated but not chain extended material is converted.

VIA

VIB

The ozonolysis reaction is similar to the ozonolytic cleavage reaction. It is carried out at low temperatures in a liquid reaction medium. The low temperature can range from a high of about 15° C. to a low equal to the freezing point of the reaction solvent, which can be as low as −100° C. or lower. Excellent results are obtained at dry ice/acetone bath temperatures (−78° C.), and a preferred temperature range is from −100° C. to about −25° C. with most preferred temperatures being in the range of from −70° C. to −80° C.

The reaction solvent employed in this reaction is again selected to assure comparability with the highly reactive ozone. The solvents employed are polar organics, preferably lower alcohols such as methanol, ethanol, the propanols and ethylene and propylene glycols; and the liquid esters such as ethyl acetate. Mixed solvents may, of course, be used. Of these solvents, the lower alcohols, and especially methanol, are preferred.

The reaction is carried out by mixing the vinyl silane in the reaction medium and then adding the ozone. The amount of ozone preferably is controlled so that excesses are avoided. Good results are obtained when the amount of ozone is limited to not more than 1.25 equivalents, based on the amount of vinylsilane present, with ozone levels of from about 0.75 to about 1.25 equivalents (based on the amount of vinylsilane present) being preferred. Lower ozone levels can be used, but are not preferred because of the lower yields which result from them.

The reaction is very quick, being complete in a few minutes at most. Excellent results are obtained at times in the range of 15 seconds to about 15 minutes, depending upon the rate of ozone delivery.

The ozonolysis reaction product is treated with acid to bring about rearrangement of transitory intermediates and give rise to the desired product tetracycles. This reaction can be carried out in an nonaqueous liquid reaction phase with halohydrocarbons such as chloroform and the like being preferred. The acid employed should be of at least moderate strength as shown by a pKa of from about 5 to about 0.1 and can be an organic or an inorganic acid. Mixtures of acids can be used, if desired. Typical acids include acetic acid; the substituted acetic acids such as trichloroacetic acid, trifluoroacetic acid and the like, and other strong organic acids such as alkyl sulfonic acids and the like. The mineral acids such as the hydrohalic acids, e.g., HCl, HBr, etc., the oxyhalo acids such as HClO₃ and the like; sulfuric acid and phosphoric acid and the like may be used as well but should be checked before use to assure that they do not cause unwanted side reactions.

The rearrangement reaction is merely catalyzed by the acid, thus in principle only a trace amount of acid is needed. However, the use of more than a trace amount of acid may be preferred. In particular, the amount of acid added is generally at least about one equivalent based on the amount of product present. Large excesses are generally not needed, and the preferred amount of acid is from about one to about ten, and especially from about one to about two, equivalents based on the amount of product present. This reaction does not require high temperatures. It will go to completion overnight at room temperature. The reaction may also proceed to completion either more rapidly or more slowly, depending on the acid and solvent system employed. Higher temperatures may be employed, if desired and if it is ascertained that they do not give unacceptable yield losses. Temperatures from about $-100°$ C. to about $+50°$ C. can be used with temperatures of from about $-20°$ C. to about $+30°$ C. being preferred and temperatures of from about $0°$ C. to about $+20°$ C. being more preferred. As would be expected, times are inversely related to temperature with times in the range of 1 hour to about 24 hours being useful.

The product of the acid-catalyzed rearrangement can be worked up and purified using chromatographic techniques and the like.

Figure 2:
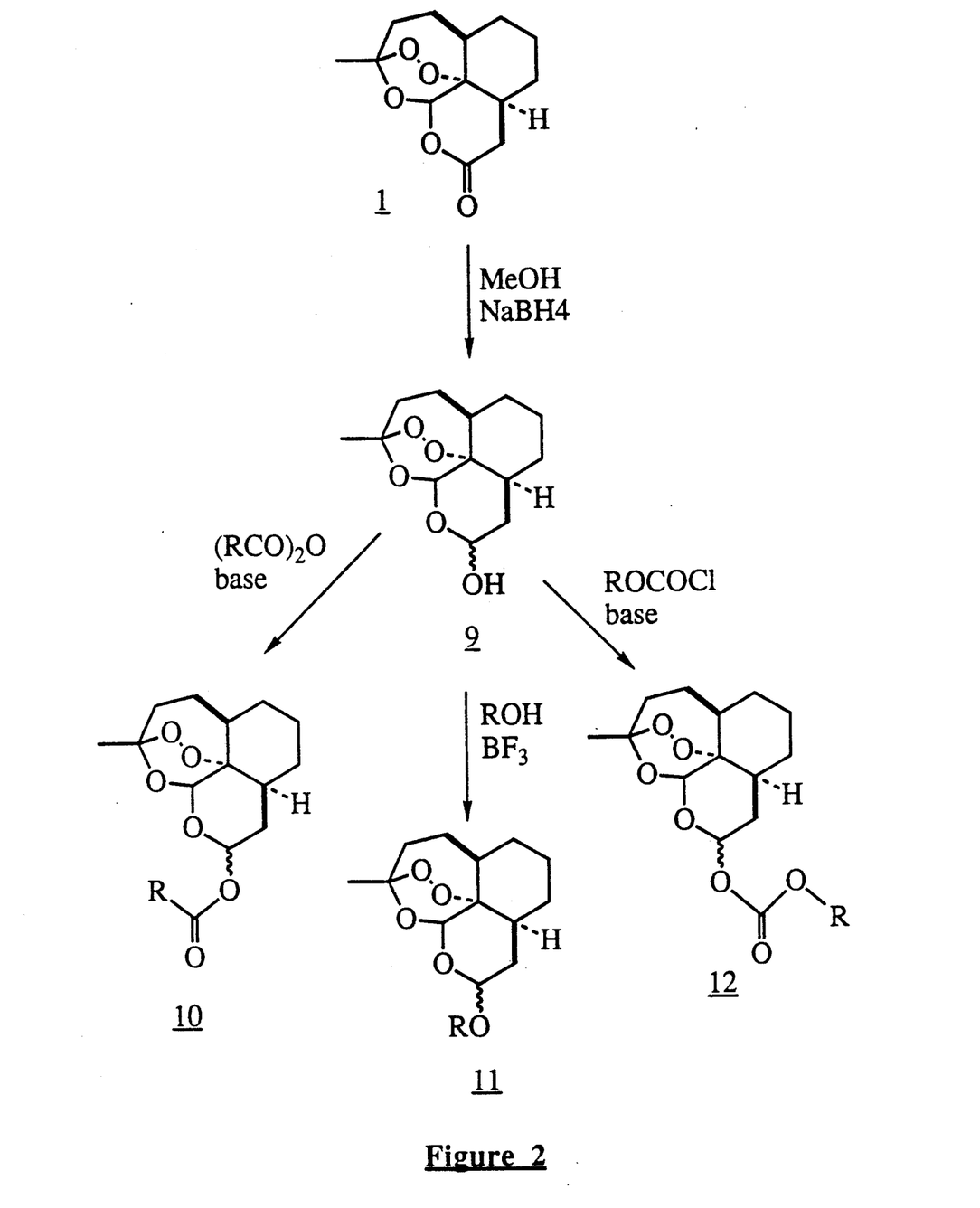
FIG. 2 is a flow scheme illustrating additional process steps for varying the X and Y substituents in the materials of the invention.

To obtain tetracycles where X and Y are other than a carbonyl oxygen, the techniques illustrated in FIG. 2 can be used. As shown in that figure, the carbonyl can be reduced without affecting the reduction-sensitive peroxy group by the use of sodium borohydride as reported by M.-m Liu et al. in *Acta Chim Sinica*, Vol 37, 129 (1979). This reduction converts the carbonyl into a lactol (hemiacetal where X is hydrogen and Y is hydroxyl). The Y hydroxyl can be converted to an ester by reaction with an appropriate acid anhydride or acid halide or active ester. Typical examples of these reactants include acetic anhydride, propionic anhydride, maleic anhydride and substituted analogs thereof, alkanoyl chlorides, and the like. This reaction is carried out in an aprotic solvent such as an ether or halohydrocarbon (for example, dichloromethane) at a moderate temperature of from about $0°$ C. to room temperature in from about 0.5 to 5 hours. An ether can also be formed such as by contacting the alcohol with methanol or a $R^*$—$CH_2$—OH alcohol corresponding to the remainder of the ether in the presence of a Lewis acid such as $BF_3$. The $BF_3$ is presented as an etherate and forms a complex with the alcohol and effects the ether formation at $-10°$ C. to room temperature in from 0.5 to 5 hours. The added alcohol is a good solvent. A carbonate can be formed from the alcohol such as by reacting it with an organic chloroformate such as an alkyl chloroformate. This is again carried out at $-10°$ C. to room temperature in from 0.5 to 5 hours in an aprotic solvent such as was used in the formation of the ester. All of these products can be recovered using a conventional organic workup.

7. The Preparation Process

The overall preparation process is the combination of the various steps provided as preparations for the various intermediates. This overall process is shown in FIG. 1. The optional steps to form the various X and Y altered materials are given in FIG. 2. The process is given as a specific reaction sequence leading to the preparation of the artemisinin analog $(+/-)$-13-,14-desmethylartemisinin and in this regard tracks the examples provided herein. It will be appreciated that by changing the starting materials as has been set forth herein, this process could be used to provide the full range of materials encompassed by General Formulas I-V. For brevity, we have not stressed the stereochemical aspects of the present process and their implications for the structure of the final tetracycle products. However, by design, the process provides a method for directing and controlling the stereochemistry of key ring positions of the final tetracycles. The control of stereochemistry is illustrated diagramatically in FIG. 1 and demonstrated in the Examples.

More particularly, the stereochemistry of the "1" and "7" centers (these centers are numbered according to their positions in artemisinin, as noted previously) is directed by the structure of the bicyclic bridging ketone. The stereochemistry remains intact through the series of reactions and directs the course of the final ozonolysis. The final ozonolysis occurs from the face of the molecule opposite the "1" and "7" substituents. This direction of the course of ozonolysis sets the stereochemistry of the "6" center so that upon the cyclization with acid the stereochemistry of the "4" and "5" centers is controlled.

An example of the possible stereochemistry of tetracycles provided by this invention is illustrated by General Formula VI**. In this formula the various R substituents and X and Y are as previously described.

General Formula VI**

The present process can provide a direct route to many artemisinin analogs previously described. In that regard, it complements the process disclosed in parent application U.S. Ser. No. 943,555. It also permits the facile synthesis of materials not readily obtainable heretofore. These are the materials of Formulas VI* and VI**, where at least one of the $R^{A1}$, $R^{A2}$, $R^{C1}$ and $R^{C2}$ substituents is other than hydrogen. These materials (and particularly when at least one of $R^{A1}$, $R^{C1}$, and $R^{C2}$ is other than hydrogen) are believed to be novel compounds.

7. Use of the Products

The artemisinin analog compounds of this invention all contain the peroxy linkage which can lead to free radical intermediates in vivo; they should have antiprotozoan activities against a broad range of parasites such as Toxoplasma, Leishmania, Trypanosoma, etc., in addition to Plasmodia. In tests they have been demonstrated to have high activity in this application. They offer activity against drug-resistant forms of malaria and can even intervene in cerebral malaria where they can interrupt coma and reduce fever. These materials should also have antihelmenthic activity against such diseases as Schistosoma and Trichinella, etc. (R. Docampo et al., *Free Radicals in Biology*, Vol. VI, Chapter 8, p. 243, 1984, Academic Press, Inc.). In this application, the compounds are generally compounded into vehicles or carriers known in the art for administration to patients in need of such treatment. The mode of administration can be oral or by injection. Typical vehicles are disclosed in *Remington's Pharmaceutical Sciences*, Alfonso R. Gennaro, ed., Mack Publishing Company, Easton, Pa. (1985).

For oral administration, the compounds can be prepared as elixirs and suspensions in sterile aqueous vehicles and also can be presented admixed with binders, carriers, diluents, disintegrants and the like as powders, as pills, or as capsules. Typical liquid vehicles include sterile water and sterile sugar syrup. Typical solid materials include starch, dextrose, mannitol microcrystalline cellulose and the like.

For administration by injection, the materials can be presented as solutions/suspensions in aqueous media such as injectable saline, injectable water and the like. They can also be presented as suspensions or solutions in nonaqueous media such as the injectable oils including injectable corn oil, peanut oil, cotton seed oil, mineral oil, ethyl oleate, benzyl benzoate and the like. The nonaqueous media can, in some cases, permit substantial quantities of the medication to be administered as a depot in the patient's fat layer so as to obtain a prolonged release of the agent to the patient.

The materials of this invention are used in fairly large doses. Commonly, dose levels of from about 100 mg/day to as much as 10,000 mg/day are employed. The actual use level will vary depending upon the particular patient's response to the drug and to the patient's degree of affliction. In a particularly preferred utility, they are used against Plasmodia and, in that use, require dosages from 0.1 to 10 times that used with the natural product artemisinin.

The peroxide link presented by all of these compounds and the free radicals it can produce are useful in a range of industrial chemical settings, as well.

8. Examples

The invention will be further described with reference being made to the following examples. These are provided merely to illustrate one preferred mode for carrying out the preparation of the invention and to illustrate several embodiments of the compounds provided by this invention and are not to be construed as a limitation upon the scope of the invention.

EXAMPLE 1

1. The total synthesis of racemic 13,14-desmethylartemisinin 1, as shown in FIG. 1.

The bicyclic ketone 2, available in good yield from cyclohexanone by the method of Still (W. C. Still, *Synthesis*, 453 (1976)), was treated with bis(trimethylsilyl)-methyl lithium to give the diene 3 in 56% yield. The disubstituted double bond of 3 was selectively converted to the ozonide by treatment with ozone in methanol:dichloromethane (1:5, v/v) in the presence of sodium bicarbonate. The crude ozonolysis product was then reacted with $Et_3N/Ac_2O$ to afford the esteraldehyde 4 in 43% yield. This unstable aldehyde was used immediately in the reaction with lithium methoxyethyldiphenylphosphine oxide (S. Warren et al, J.C.S. Perkin I, 3099 (1979)) to give a complex diastereomeric mixture of phosphine oxides 5. It was more convenient and efficient to convert 5 without prior purification to the enol ether 6 by treatment of 5 with NaH/THF. Thus, the enol ether 6 was produced from the aldehyde 4 with 54% yield. Ester hydrolysis of 6 gave the acid 7, acidification of which afforded the keto-acid 8, in 54% overall yield from 6. Finally, low temperature ozonolysis of 8 in methanol followed by careful evaporation of solvent gave an intermediate dioxetane which was treated immediately in moist $CDCl_3$ with $CF_3CO_2H$ to give the analog 1 in 33% isolated yield.

Preparation of 10-Trimethylsilylmethylenebicyclo[4.3.1]dec-2-ene (3)

Bis(trimethylsilyl)methyllithium was prepared according to a procedure of Grobel and Seebach (B.Th. Grobel and D. Seebach, Chem. Ber.,1110, 852 (1977)); to a solution of bis(trimethylsilyl)methane (2.85 ml, 13.3 mmol) in THF (20 ml) and HMPT (5 ml) at $-78°$ C. was added dropwise via syringe a solution of s-BuLi (7.66 ml of 1.74 M in pentane). The resultant pale green solution was allowed to warm to $-40°$ C. After 8 h at $-40°$ C., the resultant red solution was cooled to $-78°$ C. and a solution of bicyclo[4.3.1]dec-2-ene-10-one[2] (2.00 g, 13.3 mmol) in THF (5 ml) was added. The reaction was allowed to warm to $-5°$ C. over 13 h, then stirred with $H_2O$ (50 ml) and extracted into hexane (2×50 ml). The combined hexane layers were washed with $H_2O$ (4×100 ml) and brine (100 ml), dried over $Na_2SO_4$ and evaporated to give 3.00 g of yellow oil, which was purified via column chromatography with silica gel. After elution with EtOAc/hexane, some starting ketone, 0.35 g, was recovered and the desired diene 3 was isolated as a colorless oil, 1.64 g (56.0% yield).

NMR (400 MHz): delta 5.67 (AB pattern, 2 H, —C$\underline{H}$=C$\underline{H}$—), 5.18 (s, 1 H, =C$\underline{H}$(TMS)), 2.85 (bs, 1 H, bridgehead $\underline{H}$), 2.26 (m, 4 H, =C$\overline{H}$—C$\underline{H}_2$—), 2.05 (m, 1 H), 1.79–1.55 (m, 3 H) 1.41 (s, 1 H), 1.$\overline{28}$ (m, 1 H), 0.07 (s, 9 H, SiC$\underline{H}_3$)

Preparation of Methyl syn-2(3-(2-Acetaldehyde)-2(E.Z)trimethylsilylmethylenecyclohexyl)acetate (4)

As per Schreiber's procedure (R. E. Claus and S. L. Schreiber, *Org. Syn.*, 64, 150 (1985)), through a stirring suspension of $NaHCO_3$ (12 mg) in a solution of 10-trimethylsilylmethylenebicyclo[4.3.1]dec-2-ene (400 mg, 1.82 mmol), dry $CH_2Cl_2$ (15 ml) and absolute methanol (3 ml) at -78° C. was passed a stream of $O_3/O_2$. The disappearance of starting material was monitored by periodic TLC ($SiO_2$ in EtOAc/hex) before the mixture was purged with inert gas, allowed to warm to ambient temperature, filtered, diluted with dry benzene (30 ml) and concentrated at reduced pressure to a colorless solution of approximately 10 ml. This concentrate was diluted with dry $CH_2Cl_2$ (15 ml) and treated successively with triethylamine (0.39 ml) and acetic anhydride (0.58 ml) After 4 h at ambient temperature, the reaction was stirred with 10% aq. HCl (3 ml) and $H_2O$ (20 ml). The aqueous layer was separated and extracted with $Et_2O$ (2×25 ml). The combined organic layers were washed with $H_2O$ (25 ml), sat. aq. $NaHCO_3$ (2×30 ml) and brine (2×60 ml), dried over $Na_2SO_4$ and evaporated to give a yellow oil, which was purified via column chromatography with silica gel. After elution with EtOAc/hex, the unstable aldehyde 4 was obtained as a colorless oil, 215 mg (43.7% yield) which consisted of a 1:1 mix of E:Z isomers by NMR (90 MHz) and was used immediately.

NMR (90 MHz): delta 9.70 (m, 1 H, —C$\underline{H}$O), 5.30 (s, 1 H, =C$\underline{H}$(TMS)), 3.65 (d, 3 H, —CO$_2$C$\underline{H}_3$), 3.50–2.05 (m, 6 H), 1.90–1.10 (bm, 6 H), 0.12 (d, 9 $\overline{H}$, SiC$\underline{H}_3$)

Preparation of Methyl syn-2[3-methoxy-2(E,Z)-butenyl-2(E,Z)trimethylsilylmethylene)cyclohexyl)acetate (6)

To a solution of diisopropylamine (0.184 ml 1.31 mmol) in THF (10 ml) at 0° C. was added dropwise a solution of nBuLi (0.821 ml of 1.6 M in hexanes). After 10 min at 0° C., a solution of (1-methoxyethyl)diphenyl phosphine oxide (S. Warren et al, J.C.S. Perkin I, 3099 (1979)) (307 mg, 1.19 mmol) in THF (5 ml) was added via cannula. After 10 min at 0° C., the resultant brick red solution was cooled to −78° C., and a solution of aldehyde 4 (215 mg, 0.796 mmol) in THF (5 ml) was added via cannula. After 1 h at −78° C., the resultant yellow solution was allowed to warm to ambient temperature, stirred with sat. aq. $NH_4Cl$ (20 ml) and extracted with $Et_2O$ (2×20 ml). The combined ethereal layers were washed with sat. aq. $NH_4Cl$ (20 ml, brine (820 ml), sat. aq. $NaHCO_3$ (2×15 ml) and brine (2×25 ml), dried over $Na_2SO_4$ and evaporated to provide 483 mg of yellow foam, from which a purified sample of diastereomeric adduct mixture 5 was obtained and spectrally scrutinized.

NMR (90 MHz): delta 8.25–7.24 (bm, 10 H, Ar$\underline{H}$), 5.75–4.90 (m, 3 H, H$\underline{O}$—C$\underline{H}$), 3.67 (q, 3 H, —CO$_2$C$\underline{H}_3$), 3.30 (q, 3 H —OC$\underline{H}_3$), 3.30–0.69 (m, 15 H), 0.70 (q, 9 H, SiC$\underline{H}_3$)

The crude adduct mixture 5 was placed in THF (4 ml) and added via cannula to a stirring suspension of NaH (24 mg of an 80% oil dispersion, 0.80 mmol) in THF (8 ml). After 3 h at ambient temperature, the resultant suspension was stirred with sat. aq. $NH_4Cl$ (15 ml) and hexane (50 ml). The separated organic layer was washed with sat. aq. $NH_4Cl$ (15 ml) and brine (25 ml), dried over $Na_2SO_4$ and evaporated to afford 344 mg of orange oil, which was purified by column chromatography with silica gel. After elution with EtOAc/hexane, enol ether 6 was obtained as a colorless oil, 140 mg (54.3% yield from 4), which was a mix of four diastereomers as reflected in the NMR and TLC (SiO$_2$ in EtOAc/hexane).

NMR (90 MHz): delta 5.10 (m, 1 H, —C$\underline{H}$), 4.18 (bm, 1 H, —C$\underline{H}$(OMe)), 4.48 (m, 3 H, OC$\underline{H}_3$), 3.17–0.90.(m, 15 H), 0.07 (d, 9 H, SiC$\underline{H}_3$).

Preparation of syn-2(3(3-Oxobutyl)-2-(E,Z)-trimethyl silylmethylenecyclohexyl)acetic Acid (8)

To a solution of ester 6 (90.0 mg, 0.278 mmol) in MeOH (10 ml) was added 6 N KOH (0.69 ml, 15 equiv). The solution was heated at reflux for 12 h and allowed to stir at ambient temperature for an additional 12 h. The resultant yellow solution was acidified with sat. aq. $NH_4Cl$ (35 ml) and extracted with EtOAc (2×20 ml). The combined organic layers were washed with brine (2×30 ml), dried over $Na_2SO_4$ and evaporated to give acid 7 as a yellow oil, which was a fairly pure E:Z mix by NMR and used without further purification.

NMR (90 MHz): delta 5.23 (m, 1 H, =C$\underline{H}$), 4.26 (bt, 1 H, MeO—C=C$\underline{H}$), 3.48 (m, OC$\underline{H}_3$), 3.40–0.90 (m, 15 H), 0.07 (d, 9 H, SiC$\underline{H}_3$).

The yellow oil was placed in $CH_2Cl_2$ (10 ml) and stirred with silica gel (70–230 mesh) while adding freshly prepared 10% aq. oxalic acid (50 ml). After 2 h at ambient temperature, the solid was filtered off and rinsed with $CH_2Cl_2$ (100 ml). The filtrate was concentrated in vacuo to afford a yellow oil, which was purified by column chromatography with silica gel. After elution with HOAc/EtOAc/hexane, ketoacid 8 was obtained as a yellow oil, 77 mg (93.9% yield from 7).

NMR (90 MHz): delta 5.23 (d, 1 H, =C$\underline{H}$), 3.30–2.30 (m, 6 H), 2.13 (s, 3 H, COC$\underline{H}_3$), 2.00–1.00 (bm, 8 H), 0.07 (d, 9 H, SiC$\underline{H}_3$).

Preparation of (+)-13,14-desmethylartemisinin (1)

Through a solution of ketoacid 8 (17 mg, 0.057 mmol) in absolute MeOH (2 ml) at −78° C. was passed a stream of until no starting material could be detected by TLC (HOAc/EtOAc/hexane). The resultant pink solution was allowed to warm to ambient temperature and concentrated in vacuo to a yellow foam, which was placed in $CDCl_3$ (2 ml). After treatment with 10% trifluoroacetic acid in $CDCl_3$ (20 microliter), the formation of cyclization product 8 was monitored by NMR (90 MHz). After 8.5 h at ambient temperature, the solution was stirred with $NaHCO_3$ (25 mg), filtered, and evaporated to give 17 mg of yellow oil, which was purified by PTLC with silica gel. After development with 5% EtOAc/CHCl$_3$, the major component was isolated and reapplied to PTLC plates for development in 35% EtOAc/hexane. In this manner, (±) 13,14-desmethylartemisinin (1) was isolated as white needles which were recrystallized with EtOAc/hexane to give 4.8 mg, mp 130°–130.5° C.

$^1H$ NMR (400 MHz): delta 5.90 (s, 1 H, H$_5$), 3.18 (dd, 1 H, J = 18.3, 7.1 Hz, H$_{11alpha}$), 2.42 (dt, 1 H, J = 13.5, 3.8 Hz, H$_1$)m 2.25 (dd, 1 H, J = 18.3, 1.3 Hz, H$_{11beta}$), 2.02 (ddd, 1 H, J = 15.3, 4.9, 2.7 Hz, H$_{3alpha}$), 1.96–1.48 (m, 10 H), 1.44 (s, 3 H, —C$\underline{H}_3$). $^{13}C$ NMR: delta 168.7, 105.4, 93.2, 78.1, 43.9, 38.4, 36.0, 32.1, 31.6, 30.2, 26.6, 25.5, 25.4, 24.7. IR (KBr) 2925, 1735, 1210, 1005 cm$^{-1}$ CIMS ($^+NH_4$) m/e 272 (M+$^+NH_4$), 255 (M+$^+H$).

Biological Results

The analog 1 was sent to Walter Reed Army Institute of Research (WRAIR) for in vitro testing against P. falciparum using modifications of the procedures of Desjardins et al, 1979, and Milhous et al, 1985, (Desjardins, R. E., C. J. Canfield, D. E. Haynes, and J. D. Chulay, Antimicrob. Angents Chemother., Vol. 16, 710–718 (1979); Milhous, W. K., N. F. Weatherly, J. H. Bowdre, and R. E. Desjardins, Antimicrob. Agents Chemother. Vol. 27, 525–530, 1985.) to assess the intrinsic activity of compound 1 as an anti-malarial drug relative to simultaneous known controls such as chloroquine, mefloquine, pyrimethamine, sulfadoxine, tetracycline, qinghaosu or quinine. Since some anti-malarials are more static than cidal in action, it is necessary to extend the incubation period to assess the effects of such drugs on parasite growth rates. In order to insure exponential parasite growth and maximum uptake of radioisotope throughout the extended incubation, reduced starting parasitemias (0.2%) and reduced red cell hematocrits (1.0%) are required. As a result, drugs which are actively incorporated into erythrocytes (such as chloroquine or qinghaosu) will have slightly lower 50% inhibitory concentrations than in other assay systems employing higher red cell hematocrits. Except for the contribution from the 10% normal pooled human plasma and added 10$^{-10}$M (0.014 ng/ml) PABA, the culture medium is folate-free. The trace amount of PABA insures exponential growth of the sulfonamide-susceptible parasite clone without antagonizing the activity of antifol anti-malarials. Sulfonamides and sulfones are 1,000–10,000-fold more active and DHFR inhibitors are 5-200-fold more active in this medium than in normal RPMI 1640 culture medium.

All test compounds are solubilized in DMSO and diluted 400-fold (to rule out a DMSO effect) in culture medium with plasma for a starting concentration of at least 12,500 ng/ml. Drugs are subsequently diluted five-fold using the Cetus Pro/Pette ™ system utilizing a range of concentrations from 0.8 ng/ml to 12,500 ng/ml. Fifty percent inhibitory concentrations are reported in ng/ml.

Table 1 summarizes differences in the susceptibility profiles of the two control *P. falciparum* clones (Oduola, A. M. J., N. F. Weatherly, J. H. Bowdre, R. E. Desjardins, *Thirty-second Annual Meeting, American Society of Tropical Medicine and Hygiene, San Antonio, Texas*, Dec. 4-8, 1983) and provides results of testing. The W-2 Indochina *P. falciparum* clone is resistant to chloroquine, pyrimethamine and sulfadoxine but susceptible to mefloquine. The D-6 African *P. falciparum* clone is susceptible to chloroquine, pyrimethamine and sulfadoxine but resistant to mefloquine.

TABLE 1

IN VITRO ED$_{50}$ VALUES OF SELECTED ANTIMALARIALS AGAINST TWO STRAINS OF *P. FALCIPARUM*\*

| Antimalarial | MW | $\times 10^{-9}$ M | ng/ml | $\times 10^{-9}$ M | ng/ml |
|---|---|---|---|---|---|
| Qinghaosu | 282 | 10.99 | 3.09 | 7.01 | 1.97 |
| Dihydro-qinghaosu | 284 | 1.68 | 0.47 | 1.37 | 0.38 |
| Arteether | 312 | 6.00 | 1.87 | 3.96 | 1.23 |
| (±)-13,14-Des-methyl-artemisinin (1) | 254 | 82.95 | 21.06 | 15.98 | 4.05 |
| Chloroquine | 515 | 11.49 | 5.91 | 52.13 | 26.84 |
| Mefloquine | 414 | 53.69 | 22.22 | 3.33 | 1.37 |

\*Data obtained by Walter Reed Army Institute of Research (WRAIR)

Qinghaosu

Dihydroqinghaosu

Arteether

TABLE 1-continued (±)-13,14-Desmethyl-artemisinin (1)

The data shown in Table 1 indicate that compound 1 is approximately 1/2 as active as the natural product Qinghaosu against the W-2 Indochina strain of *P. falciparum*. Against this same strain, compound 1 was about three times as potent as the classical antimalarial agent chloroquine. While it can be seen from the table that the antimalarial efficacy of 1 varies with strain, the potency of 1 versus the other five compounds is still in the nanogram range and this is highly significant. These data show that compound 1 is a highly active antimalarial agent.

What is claimed is:

1. a polyoxatetracyclic compound of the formula wherein the R's are each independently selected from the group consisting of hydrogen and a lower alkyl of 1 to 4 carbon atoms and X and Y are selected such that they together equal a carbonyl oxygen or X is a hydrogen while Y is selected from the group consisting of hydrogen, hydroxyl, alkyloxy, alkylcarbonyloxy, hydroxycarbonyloxy, alkylaminocarbonyl, alkylaminocarbonyloxy and ureido.

2. The polyoxatetracyclic compound of claim 1 wherein $R^{B1}$ and $R^{B2}$ are each hydrogen.

3. The polyoxatetracyclic compound of claim 2 wherein $R^F$ is hydrogen.

4. The polyoxatetracyclic compound of claim 3 wherein R is $CH_3$.

5. The polyoxatetracyclic compound of claim 4 wherein $R^{A2}$ and both $R^{C1}$s and $R^{C2}$s are hydrogen such that the compound is (±)-13,14-desmethylartemisinin.

6. An antimalarial composition comprising an effective malaria-treating amount of the compound of claim 1 in a pharmaceutically acceptable carrier.

7. A method for treating malaria which comprises administering to a patient in need of such treatment an effective malaria treating dose of the composition of claim 6.

8. An antimalarial composition comprising an effective malaria-treating amount of the compound of claim 5 in a pharmaceutically acceptable carrier.

9. A method for treating malaria which comprises administering to a patient in need of such treatment an effective malaria treating dose of the composition of claim 8.

* * * * *